United States Patent

Day

[11] Patent Number: 5,693,797
[45] Date of Patent: Dec. 2, 1997

[54] PROCESS FOR PREPARING BROMINATED PHTHALIMIDES

[75] Inventor: James F. Day, Winston-Salem, N.C.

[73] Assignee: Unitex Chemical Corporation, Greensboro, N.C.

[21] Appl. No.: 800,337

[22] Filed: Feb. 14, 1997

[51] Int. Cl.[6] ............... C07D 403/14; C07D 209/48
[52] U.S. Cl. .................. 544/198; 548/461; 548/462; 548/473; 548/476; 548/478; 548/480; 548/513
[58] Field of Search .............. 544/198; 548/461, 548/462, 473, 476, 478, 480

[56] References Cited

U.S. PATENT DOCUMENTS

| | | | |
|---|---|---|---|
| 3,873,567 | 3/1975 | Cyba | 260/326 |
| 4,053,528 | 10/1977 | Thorpe | 260/648 |
| 4,374,220 | 2/1983 | Sonnenberg | 524/94 |
| 4,894,187 | 1/1990 | Bonnet et al. | 252/609 |
| 4,997,953 | 3/1991 | McKenna | 548/461 |
| 5,025,050 | 6/1991 | Torres | 524/91 |
| 5,076,970 | 12/1991 | Roos et al. | 252/609 |
| 5,137,948 | 8/1992 | Bonnet et al. | 524/90 |
| 5,175,305 | 12/1992 | Roos et al. | 548/461 |
| 5,290,945 | 3/1994 | Roy et al. | 548/462 |
| 5,317,048 | 5/1994 | Tarbit et al. | 524/94 |
| 5,508,429 | 4/1996 | Tarbit et al. | 548/462 |

OTHER PUBLICATIONS

Sydney M. Spatz et al.; Use of Tetrabromophthalic Anhydride (TBPA) In The Construction Of Fire–Retardant Polyester And Epoxy Resins; Dec. 1969; 381–391.

*Primary Examiner*—Michael G. Ambrose
*Attorney, Agent, or Firm*—Olive & Olive, P.A.

[57] ABSTRACT

A process for the preparation of brominated phthalimides that involves mixing tetrabromophthalic anhydride, an organic acid, and an organic dispersing agent in water at approximately 110° C. under 1 bar pressure is disclosed. An amine is added and the reaction mixture is stirred for six hours under approximately 5 bar pressure and heated at least to 120° C. The reactant mass is washed in water and then methanol. The process decreases production time, increases whiteness and purity, and decreases yellowness and particle size of the resulting product.

29 Claims, No Drawings

PROCESS FOR PREPARING BROMINATED PHTHALIMIDES

BACKGROUND OF THE INVENTION

1. Field of the Invention

This invention relates to improved methods for preparing highly white brominated phthalimides for use as flame retardants by charging a pressure reaction chamber with at least tetrabromophthalic anhydride, water, an organic acid, an acidic dispersing agent, and an amine and maintaining the reaction mass at approximately 150° C. for approximately six hours.

2. Description of the Related Art

This invention relates to the process of preparing brominated phthalimides. Brominated phthalimides are often used as flame retardants as well as plasticizers in various applications. One example is brominated phthalimides use in polymeric compositions for primary insulation and protective jacketing for electrical conductors. Other examples include use of brominated phthalimides in PET (Polyethylene terephthalate), PBT (Polybutylene terephthalate), polycarbonate, Nylon 6, 6/6, 11, and 12, polyethylene, HIPS (High Impact Polystyrene), ABS (Acrylonitrile/Butadiene/Styrene terpolymer), EPDM (Ethylene/Prolylene/Dienerubber), silicone rubber paints, hot melt adhesives, thermoset resins (e.g. epoxy, phenolic, unsaturated polyester, and vinyl esters). The color of tetrabromophthalimide flame retardants pigment the plastics in which they are added. Therefore, flame retardants of the highest white indices are preferred.

A number of patents describe processes for preparing brominated phthalimides. For example, U.S. Pat. No. 4,997,953 (the "953 patent") of McKenna describes a process for preparing N,N'-bis(tetrabromophthalimide) by forming a reaction mass from tetrabromophthalic anhydride and hydrazine in concentrated sulfuric acid. The reaction mass was heated at 180° C. for 14 hours. The end product is approximately 95% by weight N,N'-bis (tetrabromophthalimide). The McKenna process requires a strong environmentally unfriendly inorganic acid as the solvent, which must ultimately be washed from the reaction mass and disposed. In addition, strong acid solvents require special processing equipment, resulting in corrosion and contamination of product with metals, such as iron, chromium and nickel. Residual sulfuric acid also causes phthalimide instability. The McKenna process requires long reaction times and produces a product having an unsatisfactory whiteness index.

U.S. Pat. No. 5,076,970 of Ross et al. discloses making N,N'-bis(tetrabromophthalimide) by using the process described in the '953 patent. However, it treats the N,N'-bis (tetrabromophthalimide) product with a base such as sodium hydroxide. The '970 patent reports a significant drop in acid number resulting in a significant increase in the stability of bis-phthalimide product. In addition, base treatment results in decreased particle size of the bis-phthalimide product. However, the reaction time is not reduced, the product whiteness remains unsatisfactory and use of an inorganic acid solvent is not eliminated.

Roy et al. (U.S. Pat. No. 5,290,945) describes a method for production of N,N' bis (tetrabromophthalimide) or N,N'-alkylene-bis (tetrabromophthalimide) by mixing tetrabromophthalic anhydride and a diamine of hydrazine (which can be added neat or in a solvent comprising xylene) in a solvent that includes at least 15% by weight organic acid (mono-di- or tri-carboxylic acid) and other constituents such as xylene. The invention of the '945 patent continues to use exotic solvents.

U.S. Pat. No. 5,137,948 of Bonnet et al. claims a process comprising, in part, reacting hydrazine and a halogenated dicarboxylic acid anhydride in an acidic aqueous medium. However, Bonnet merely describes (Example 2) mixing sulfuric acid to an aqueous suspension of tetrabromophthalic anhydride to produce a product that contains only 29% N,N'-bis(tetrabromophthalimide).

U.S. Pat. No. 5,317,048 of Tarbit et al. describes a process for the preparation of N,N'-ethylene-bis-(tetrabromophthalimide). The Tarbit process involves reacting two moles of tetrabromophthalic anhydride with 1 mole of ethylene diamine in 99% acetic acid with very low acetic anhydride content and heating the mixture at 160° C. for 18 hours. The '048 process notes that an acetic acid medium having a preferred water content of less than 0.1% is essential to the production of its N,N'-ethylene-bis (tetrabromophthalimide). Removal of water during the '048 process demonstrates that phthalimide chemistry involves condensation with, traditionally, removal of water. The process of Tarbit et al. has the disadvantages of using an acidic solvent and requiring a long 18 hour reaction time.

The aforesaid '953, '970, '945, '948 and '048 patents are to be deemed incorporated herein by reference.

Accordingly, the primary object of this invention is to be able to mix organic acid, an acidic dispersing agent, tetrabromophthalic anhydride, and an amine in an aqueous medium to make a highly white product with ultra-low acid values and small particle size in a reaction time about two-thirds of the reaction time of the fastest traditional methods. Traditionally, processes for making brominated phthalimides have required long reaction times and produce products characterized by unacceptably high yellowness and low whiteness indexes. Other objects and advantages will be more fully apparent from the following disclosure and appended claims.

SUMMARY OF THE INVENTION

The invention is an improved process for the preparation of brominated phthalimides. Unlike prior art processes, the process of the invention uses an acidic dispersing agent to provide smaller product particle size and decreased reaction time to form a highly white product. According to the process of the invention, tetrabromophthalic anhydride is mixed with organic acid, an acid dispersing agent, and water to 110° C. and 1 bar pressure. An amine is added over 30 minutes and the reaction mass is then heated, and stirred, to 150° C. for 6 hours. The reaction is then cooled, filtered, and washed with hot water and methanol. The resulting product contains approximately 97% bis-tetrabromophthalimide with a whiteness index of 84.3 and a yellowness index of 1.85. The process of the invention decreases treatment time, decreases product particle size, decreases the yellowness index, and increases the whiteness index of the brominated phthalimide product.

DETAILED DESCRIPTION OF THE INVENTION AND PREFERRED EMBODIMENTS THEREOF

For purposes of disclosure, a brominated phthalimide is represented by the following formula where $y=1-4$ and R=alipathic, aromatic or heterocyclic moiety:

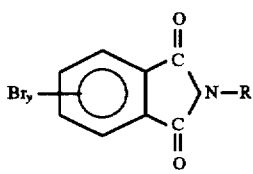

The process of the invention comprises mixing in a 50 gallon stainless steel pressure reactor an organic acid selected from a group consisting of formic acid, acetic acid and propionic acid with an acidic dispersing agent and tetrabromophthalic anhydride in water. The preferred organic acid for the method of this invention is propionic acid. This initial mixture contains approximately 80% water by weight. The acidic dispersing agents are selected from a group consisting of: (1) benzene, 1,1-oxybis, tetrapropylene derivatives, sulfonated, sodium salts (CAS RN 119345-04-9, distributed by Dow Chemical Company under the name Dowfax 2A1); (2) poly(oxy-1,2-ethanediyl),alpha-(nonylphenyl)-omega-hydroxy-, branched phosphates (CAS RN 68412-53-3, distributed by Rhone-Poulenc under the name Rhodafac RE610), and (3) poly(oxy-1,2-ethanediyl), -alpha-(dinonylphenyl)-omega-hydroxy-, phosphate (CAS RN 39464-64-7 distributed by Rlaone-Poulenc under the name Rhodafac RM-510). The solution is heated to 110° C. at 1 bar pressure. An amine is selected from the group consisting of hydrazine, monoamine, substituted monoamine, diamines, substituted diamines, triamines, and substituted triamines. For example, aqueous hydrazine is added to the solution over a thirty minute period to form a reactant mass. The reactant mass is stirred for 6 hours and 5 bar pressure at 150° C. The reactant mass may be heated to approximately between 120° to 170° C., but the preferred temperature is between 150° and 170° C. The molar ratio of hydrazine to tetrabromophthalic anhydride in the mixture is approximately 1:2. The mixture is cooled to 80° C., filtered and washed in hot water and then in methanol. A vacuum at 120°–140° C. is applied to make a dry filter cake. The product obtained using hydrazine contains 97% bis (tetrabromophthalimide) with 0.1% tetrabromophthalic anhydride and 2.9% N-aminotetrabromophthalimide. The bis (tetrabromophthalimide) product has an acid number of 0.23 mgKOH/g sample. The whiteness index of the product was recorded as 84.3 and yellowness index at 1.85.

It is believed that the acidic dispersing agents act as phase transfer catalysts, transferring the amines from the aqueous phase into an emulsion of tetrabromophthalic anhydride. It was discovered that a quantity up to 10% acidic dispersing agents by weight of the water, organic acid, and tetrabromophthalic anhydride mixture was effective. It was also discovered that the higher the concentration of acidic dispersing agent used the smaller the product particle size. However, the process becomes less economically sound as more dispersing agent is added. The acidic dispersing agents speed up reaction time and also cause a decrease in product particle size which traps less impurities into the end product. In contrast, larger particles produced by traditional methods trap impurities which negatively affect plastics' performance characteristics, including having a negative effect on plastics' electrical insulation and UV stability. Small particle size is also critical to achieve optimum dispersion of the flame retardant in plastics at the lowest loading levels.

The acidic dispersing agents identified above are all anionic dispersing agents. It was found that cationic dispersing agents are neutralized in acidic aqueous media of the invention and lose their surfactant activity. Non-ionic dispersing agents were found not to react as a catalyst and seem to decompose in the acidic aqueous media. Anionic acidic dispersing agents, therefore, appear to be the stable surfactant under acidic/aqueous conditions. Omitting the dispersing agent from the reaction mass slowed reaction rates, increased product particle size, and increased impurities trapped within the product particle.

By way of a brief description of the process reactions, the organic acid and the tetrabromophthalic anhydride react to form phthalic acid intermediaries which can react with amines to form amide intermediates. The amide intermediates dehydrate to form n-aminotetrabromophthalimide which can react with the phthalic acid intermediary to form a bis-coupled adduct intermediary which dehydrates to form a brominated phthalimide product.

The general reaction scheme for the process of preparing brominated phthalimides can be represented by the following formulae where R=aliphatic, aromatic or heterocyclic moieties and Y=1–4. It is understood that descriptions of the process reactions are for illustrative purposes only and are not to be taken as limiting the scope of the invention.

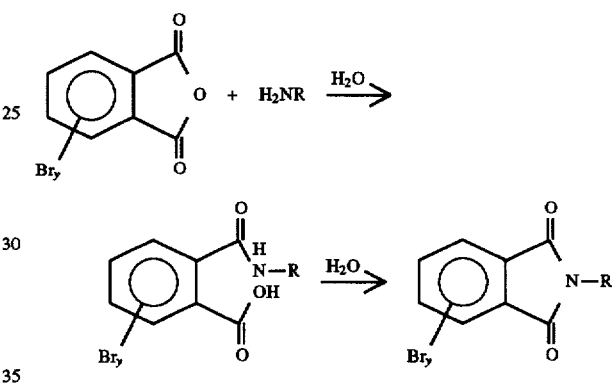

The following formulae represent the general process reactions using hydrazine.

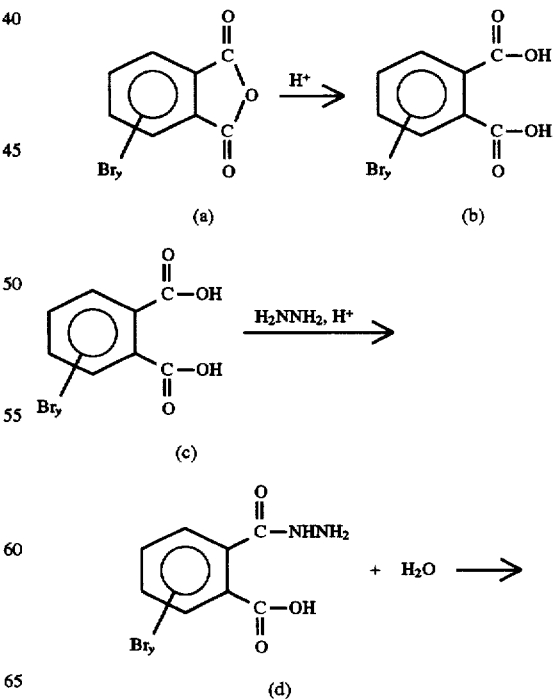

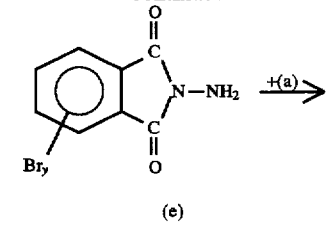

(e)

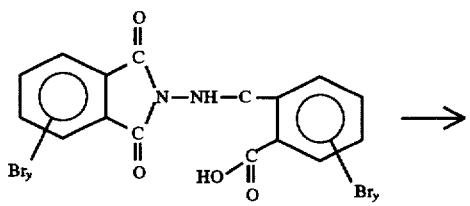

(f)

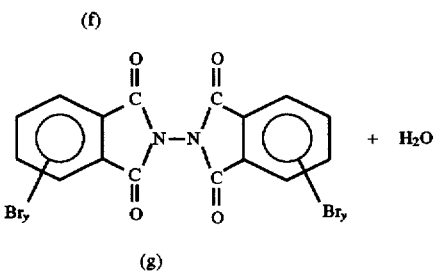

(g)

It is understood that the following Examples are also for illustrative purposes only and are not to be taken as limiting the scope of the invention.

EXAMPLE 1

Preparation of N,N-Bis(tetrabromophthalimide)

Into the 50 gallon stainless steel pressure reactor was charged 240 pounds of water, 60 pounds tetrabromophthalic anhydride, 2 pounds propionic acid, and 2 pounds of the acidic dispersing agent Dowfax 2A1. The mixture was stirred at 110° C. and 1 bar pressure. The reactor was then charged with 50 pounds 4.2% aqueous hydrazine solution over 30 minutes (the molar ratio of tetrabromophthalic anhydride to hydrazine was 2:1). The reaction mass was then heated to 150° C. under 5 bar pressure for 6 hours. The reaction mass was then cooled to 80° C., filter washed with 60 pounds hot water and then 30 pounds of methanol. The filter cake was then vacuum dried at 120°–140° C. The product of Example 1 showed the following properties:

| | |
|---|---|
| Bis-tetrabromophthalimide | 97% |
| Tetrabromophthalic anhydride | 0.1% |
| N-aminotetrabromophthalimide | 2.9% |
| Acid number (mg KOH/g sample) | 0.23 |
| Whiteness index | 84.3 |
| Yellowness index | 1.85 |

EXAMPLE 2

The process of Example 2 is the same as the process in Example 1. However, in Example 2 the reactor was charged with 8 pounds monoethanolamine, in place of the hydrazine, diluted in 50 pounds of water over 30 minutes. The yield was 60 pounds of a highly white powder, having less than 0.1% residual tetrabromophthalic anhydride, with the following additional properties:

| | |
|---|---|
| N-hydroxyethyltetrabromophthalimide | 98.1% |
| Acid Number (mg KOH/g sample) | 0.16 |
| Melting Point | 258–261° C. |

EXAMPLE 3

Into the 50 gallon stainless steel reactor was charged 300 pounds water, 2 pounds propionic acid, 2 pounds acidic dispersing agent, and 30 pounds tetrabromophthalic anhydride. The mixture was heated and stirred at 110° C. and 1 bar pressure. The reactor was then charged with 22 pounds molten 2,4,6-tribromoaniline over 30 minutes. The remaining process steps of Example 3 are as stated in Example 1. The yield was 50 pounds of a highly white powder with the following properties:

| | |
|---|---|
| Acid Number (mg KOH/g sample) | 0.1 |
| N-(2',4',6'-Tribromophenyl)tetrabromophthalimide | 97% |
| Tetrabromophthalic anhydride | 0.1% |
| 2,4,6-Tribromoaniline | 2.4% |

EXAMPLE 4

The process of Example 4 is the same as the process in Example 1. However, in Example 4 instead of charging the reactor with hydrazine, the reactor was charged with a melamine adduct prepared by mixing 3.05 moles tetrabromophthalic anhydride with 1 mole melamine. The end product had the following properties:

| | |
|---|---|
| Tris(tetrabromophthalimide)melamine | |
| Bis-tetrabromophthalimide | 99% |
| Acid Number (mg KOH/g sample) | 0.24 |
| Tetrabromophthalic anhydride | 0.1% |
| Whiteness index | 69.1 |
| Yellowness index | 6.2 |

EXAMPLE 5

The process of Example 5 is the same as the process in Example 1, except 50 pounds of 7.89% aqueous ethylene diamine was added for the amine. The product of Example 5 had the following properties:

| | |
|---|---|
| N,N-Ethylene-bistetrabromophthalimide | 98.1% |
| Tetrabromophthalic anhydride | 0.1% |
| N-Aminoethyltetrabromophthalmide | 1.8% |
| Acid number (mg KOH/g sample) | 0.21 |
| Whiteness index | 84.8 |
| Yellowness index | 1.9 |
| Melting Point: greater than 450° C. | |

COMPARATIVE EXAMPLE 6

The process of Example 6 is the same as the process of Example 1. However, Example 6 does not include the organic acid or the acid dispersing agent and uses a molar ratio of hydrazine to tetrabromophthalic acid anhydride of 1:1. The stainless steel 50-gallon reactor was charged with 240 pounds of water and 67.2 pounds of tetrabromophthalic acid anhydride and was stirred and heated to 115° C. A 10% aqueous hydrazine solution of 44 pounds was added while maintaining the temperature at 115° C. and then raised to 130° C. and stirred for 8 hours at 5 bar pressure. The reaction mixture was cooled to 80 C, filtered and filter cake washed with water to pH 7. The vacuum dried filter cake melted at 120°–140° C.; yield (60 pounds) of off-white powder. The product of Example 6 showed the following properties:

| Bis-tetrabromophthalimide | 54.5% |
|---|---|
| Tetrabromophthalic anhydride | 45.4% |
| Acid number (mg KOH/g sample) | 109 |
| Whiteness Index | 69.3 |
| Yellowness Index | 10.4 |

COMPARATIVE EXAMPLE 7

The process of Example 7 is the same as that of Example 6. However, 6.4 pounds of 100% hydrazine was added such that the ratio of tetrabromophthalic anhydride to hydrazine was 2:1. The reactor was sampled at 8, 16, and 24 hours.

| | Reaction time (hours) | | |
|---|---|---|---|
| | 8 | 16 | 24 |
| Bis-tetrabromophthalimide | 65.1 | 84.3 | 91.8 |
| N-Aminotetrabromophthalimide | 26.1% | 11.2% | 6.9% |
| Tetrabromophthalic anhydride | 8.8% | 4.5% | 1.4% |
| Acid number (mg KOH/g sample) | 21.1 | 10.9 | 3.1 |
| Whiteness Index | 68.3 | 64.1 | 62.2 |
| Yellowness Index | 12.2 | 16.3 | 18.4 |

COMPARATIVE EXAMPLE 8

Example 8 repeated Example 7 with 2 pounds of acetic acid mixed for 24 hours. The product of Example 8 showed the following properties:

| Bis-tetrabromophthalimide | 90.0% |
|---|---|
| Tetrabromophthalic anhydride | 1.4% |
| N-Aminotetrabromophthalimide | 7.7% |
| Acid number (mg KOH/g sample) | 3.4 |
| Whiteness index | 84.3 |
| Yellowness index | 4.84 |

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A process for the preparation of brominated phthalimides comprising the steps of reacting tetrabromophthalic anhydride, an organic acid, an acidic dispersing agent, and an amine in water for a sufficient time to form said brominated phthalimides.

2. The process of claim 1, wherein said acidic dispersing agent is an anionic dispersing agent.

3. The process of claim 1, wherein said acidic dispersing agent is selected from the group consisting of benzene, 1,1'-oxybis-; tetrapropylene derivatives, sulfonated, sodium salts; poly(oxy-1,2-ethanediyl),alpha-(nonylphenyl)-omega-hydroxy-, branched phosphates; and poly(oxy-1,2-ethanediyl),-alpha-(dinonylphenyl)-omega-hydroxy-, phosphates.

4. The process of claim 1, wherein the molar ratio of anhydride/amine is approximately 2:1.

5. The process of claim 1, wherein the reaction is carried out under pressure at a temperature of at least 120° C.

6. The process of claim 1, wherein the reaction is carried out under pressure at a temperature between approximately 150°–170° C.

7. The process of claim 1, wherein said organic acid is selected from the group consisting of formic acid, acetic acid, and propionic acid.

8. The process of claim 1, wherein said amine is selected from the group consisting of hydrazine, monoamines, substituted monoamines, diamines, substituted diamines, triamines, and substituted triamines.

9. The process of claim 1, wherein said amine is 2,4,6-tribromoaniline.

10. The process of claim 1, wherein said amine is hydrazine.

11. The process of claim 1, wherein said amine is monoethanolamine.

12. The process of claim 1, wherein said amine is melamine.

13. A process for the preparation of brominated phthalimides comprising the steps of:
    a. reacting tetrabromophthalic anhydride, organic acid, and an acidic dispersing agent in water to form a mixture;
    b. heating said mixture to at least 110° C. under a first pressure;
    c. adding an amine selected from a group comprised of hydrazine, monoamines, substituted monoamines, diamines, substituted diamines, triamines, and substituted triamines to said mixture to form a reactant mass having a molar ratio of anhydride/amine of 2:1;
    d. heating said reactant mass to at least 120° C.; and
    e. stirring said reactant mass under a second pressure for a period of time to yield said brominated phthalimide.

14. The process of claim 13, wherein said first pressure is approximately 1 bar pressure.

15. The process of claim 13, wherein said second pressure is approximately 5 bar pressure.

16. The process of claim 13, wherein said period of time is approximately 6 hours.

17. The process of claim 13, wherein said reactant mass is heated to approximately 150°–170° C.

18. The process of claim 13, wherein said water is about 80% by weight of said mixture.

19. The process of claim 13, wherein said acidic dispersing agent is selected from the group consisting of benzene, 1,1'-oxybis-, tetrapropylene derivatives, sulfonated, sodium salts; poly(oxy-1,2-ethanediyl),alpha-(nonylphenyl)-omega-hydroxy-, branched phosphates; and poly(oxy-1,2-ethanediyl),-alpha-(dinonylphenyl)-omega-hydroxy-, phosphates.

20. The process of claim 13, wherein said organic acid is selected from the group consisting of formic acid, acetic acid, and propionic acid.

21. The process of claim 13, wherein said amine is monoethanolamine.

22. The process of claim 13, wherein said amine is 2,4,6-tribromoaniline.

23. The process of claim 13, wherein said amine is hydrazine.

24. The process of claim 13, wherein said amine is melamine.

25. A process for the preparation of bis (tetrabromophthalimide) comprising the steps of:
    a. providing a reactor,
    b. charging said reactor with 240 pounds of water, 2 pounds of organic acid, 2 pounds of acidic dispersing agent selected from the group consisting of benzene, 1,1'-oxybis-, tetrapropylene derivatives, sulfonated, sodium salts; poly(oxy-1,2-ethanediyl),alpha-(nonylphenyl)-omega-hydroxy-, branched phosphates; and poly(oxy-1,2-ethanediyl),-alpha-(dinonylphenyl)-omega-hydroxy-, phosphates, and 60 pounds of tetrabromophthalic anhydride to form a mixture;

c. heating while stirring said mixture to approximately 100° C. at approximately 1 bar pressure;

d. adding hydrazine to said mixture for approximately 30 minutes to form a reactant mass having a molar ratio of anhydride/amine of 2:1;

e. heating said reactant mass to 120°–170° C.;

f. stirring said reactant mass for approximately 6 to 15 hours;

g. cooling said reactant mass;

h. filter washing said reactant mass with hot water and then methanol; and i. vacuum drying said reactant mass to form a very white powder bis (tetrabromophthalimide) product.

26. A process of claim 25, wherein said reactant mass is heated to approximately 150°–170° C.

27. A process of claim 25, wherein the reactant mass is stirred for approximately 6 hours.

28. A process of claim 25, wherein said product has a whiteness index of approximately 84.3 and a yellowness index of approximately 1.85.

29. A process of claim 25, wherein said product is approximately 97% bis-tetrabromophthalimide, 0.1% tetrabromophthalic anhydride, and 2.9% N-aminotetrabromophthalimide.

* * * * *

UNITED STATES PATENT AND TRADEMARK OFFICE
CERTIFICATE OF CORRECTION

PATENT NO. : 5,693,797
DATED : December 2, 1997
INVENTOR(S) : James F. Day

Page 1 of 2

It is certified that error appears in the above-indentified patent and that said Letters Patent is hereby corrected as shown below:

In column 5, line 15, please delete the following chemical structure:

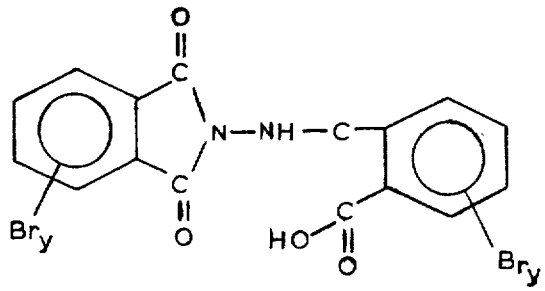

and substitute therefore, the following corrected chemical structure:

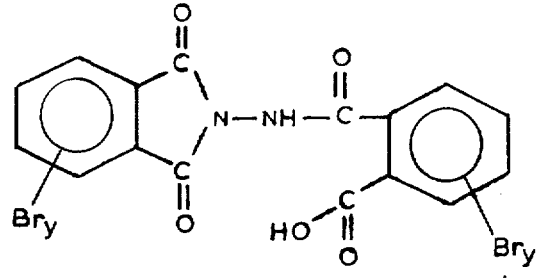

UNITED STATES PATENT AND TRADEMARK OFFICE
CERTIFICATE OF CORRECTION

PATENT NO. : 5,693,797
DATED : December 2, 1997
INVENTOR(S) : James F. Day

It is certified that error appears in the above-identified patent and that said Letters Patent is hereby corrected as shown below:

In column 6, line 67, please delete the period following the capital letter "C".

In column 7, line 1, please delete the period following the capital letter "C".

In column 7, line 4, please delete the period following the capital letter "C".

In claim 3, please delete the semicolon that follows "1,1' oxybis-".

Signed and Sealed this

Seventeenth Day of February, 1998

BRUCE LEHMAN

Attest:

Attesting Officer

Commissioner of Patents and Trademarks